United States Patent [19]

Brion et al.

[11] Patent Number: 5,278,322

[45] Date of Patent: Jan. 11, 1994

[54] PROCESS

[75] Inventors: Francis Brion, Gagny; Colette Colladant, Rosny Sous Bois; Jacques Lagouardat, Noisy Le Grand; Jacques Scholl, Romainville, all of France

[73] Assignee: Roussel Uclaf, France

[21] Appl. No.: 968,429

[22] Filed: Oct. 29, 1992

[30] Foreign Application Priority Data

Nov. 8, 1991 [FR] France ............... 91 13775

[51] Int. Cl.$^5$ ............... C07D 311/02; C07C 61/04
[52] U.S. Cl. ............... 549/285; 549/287; 549/313; 562/506
[58] Field of Search ............... 549/313, 285, 287; 562/506

[56] References Cited

U.S. PATENT DOCUMENTS

| | | | |
|---|---|---|---|
| 2,726,250 | 12/1955 | Clauson-Kaas | 549/313 |
| 3,694,472 | 9/1972 | Martel et al. | 562/506 |
| 3,965,129 | 6/1976 | Perry et al. | 549/313 |
| 4,014,918 | 3/1977 | Martel | 560/124 |
| 4,390,724 | 6/1983 | Martel et al. | 549/313 |
| 4,435,597 | 3/1984 | Arlt | 562/506 |
| 4,487,957 | 12/1984 | Martel et al. | 549/313 |
| 4,518,797 | 5/1985 | Romen | 562/506 |

FOREIGN PATENT DOCUMENTS

| | | |
|---|---|---|
| 1580474 | 9/1969 | France . |
| 527152 | 10/1972 | France . |
| 2396006 | 1/1979 | France . |
| 2002377 | 2/1979 | United Kingdom . |

OTHER PUBLICATIONS

Copy of Agr. Biol. Chem. vol. 29, No. 9 pp. 784-786 1965.
Copy of Search Report (3 pages).
Copy of Methoden Der Organischen Chemie 1981 (5 pages) TEIL 1.
Copy of Methoden Der Organischen Chemie 1975 TEIL 2 (5 pages).

*Primary Examiner*—C. Warren Ivy
*Assistant Examiner*—Raymond Covington
*Attorney, Agent, or Firm*—Bierman and Muserlian

[57] ABSTRACT

A process for the preparation of a compound of the formula

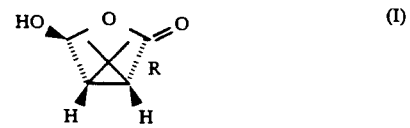

comprising reacting 1R, cis 2,2-dimethyl 3-(2-oxo-propyl)-cyclopropane-1-carboxylic acid with an alkali metal, alkaline-earth metal or magnesium hypohalite, and oxidizing the 1R, cis 2,2-dimethyl 3-(hydroxy-carboxy-methyl)-cyclopropane-1-carboxylic acid or its salt or lactonic form thereof thus obtained with an oxidizing agent to obtain the compound of formula I and novel intermediates.

18 Claims, No Drawings

PROCESS

STATE OF THE ART

Related prior art includes British Patent Application No. 2,002,377 and Swiss Patent No. 527,152 and Houben-Weyl, Methoden der Organischen Chemie, Vol. 4/1A page. 435 to 640 (1981) and vol. 4/1B, page 415 to 424 (1975).

OBJECTS OF THE INVENTION

It is an object of the invention to provide a novel process for the preparation of the lactone of 1R,cis 2,2-dimethyl-3-formylcyclopropne carboxylic acid and novel intermediates.

This and other objects and advantages of the invention will become obvious from the following detailed description.

THE INVENTION

The novel process of the invention for the preparation of a compound of the formula

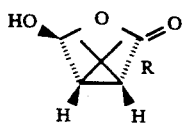

comprises reacting a compound of the formula

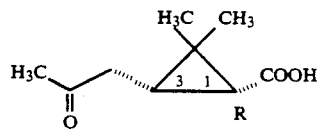

1R,cis configuration with an alkali metal, alkaline-earth metal or magnesium hypohalite to obtain a compound of the formula

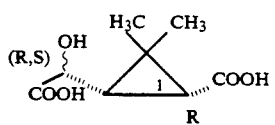

of 1R,cis configuration, also able to exist in the lactonic cyclized form

one or other form appearing as a mixture of diastereoisomers and in the form of an alkali metal, alkaline-earth metal or magnesium salt, optionally isolating the acid, then optionally isolating the diastereoisomers, then reacting the compound of formula III or III' in the form of a mixture of diastereoisomers or of separate diastereoisomers or its salt with an oxidizing agent to obtain the compound of formula I.

The alkali metal, alkaline-earth metal or magnesium hypohalite may be sodium, potassium, lithium, calcium or magnesium hypochlorite, hypobromine or hypoiodite, and preferably sodium hypochlorite.

In the preferred conditions for the process of the invention, at least 4 equivalents of the alkali metal or alkaline-earth metal hypohalite and particularly sodium hypochlorite are used and the operation takes place at a temperature of $-10°$ to $+20°$ C. and preferably $-5°$ to $+5°$ C. in aqueous phase. Moreover, it may be advantageous to operate in the presence of a basic agent which can be selected from the group consisting of alkali metal and alkaline-earth metal hydroxides and preferably sodium, potassium and calcium hydroxides.

The optional separation of the diastereoisomer of formula III or III' can be carried out by standard means, notably chromatography or crystallization. Examples are described hereafter in the experimental part.

The isolation of the acid of formula III or III' can be carried out by acidification of the reaction medium, preferably after neutralization of the oxidizing agent by a reducing agent, for example sodium thiosulfate, then extraction by standard means. Isolation of the salt is possible by bringing the reaction medium to dryness, preferably after neutralization of the oxidizing agent.

The oxidizing agent with which the compound of formula III or III' is treated can be selected from the group consisting of hypohalous acids, alkali metal, alkaline-earth metal and magnesium hypohalites, potassium permanganate, chromic acid, periodic acid and alkali metal bismuthates. It can also be manganese dioxide or a perborate. A hypohalous acid and preferably hypochlorous acid is more particularly preferred.

In the preferred conditions for the process, the hypohalous acid used as oxidizing agent is obtained in situ from an alkali metal, alkaline-earth metal or magnesium hypohalite placed in an acid medium. The hypochlorous acid is thus obtained in situ from sodium hypochlorite. The acid used to liberate the hypochlorous acid is preferably selected from the group consisting of lower alkanoic acids such as acetic acid or propionic acid, as well as solutions of phosphates, borates and acetates of appropriate pH.

Preferably the process takes place without the intermediate isolation of the compound of formula III or III'. In this case, the operating conditions and especially the oxidizing agent used can be the same as those which have been defined above. However, the use of a hypohalous acid or an alkali metal or alkaline-earth metal hypohalite is particularly preferred. Then, the operation is advantageously carried out by using at the start a quantity which is greater than 4 equivalents of hypohalite, particularly sodium hypochlorite.

The process which consists of putting the product of formula II in the presence of the hypohalite alone, therefore acting also as an oxidizing agent, is within the framework of the invention. Such a process is illustrated in the experimental part.

The starting compound of formula II is known from Agr. Biol. Chem., Vol. 29, No. 8, p. 784 (1965).

It can be specified purely for information and in a non-limitative manner that the action of the hypohalite in aqueous medium on the compound of formula II involves the formation in situ of mono- and polyhalogenated compounds on the chain in the 3-position, these constituting intermediates in the formation of the compound of formula III or III'. These intermediate compounds are described in copending patent Ser. No. 964,500.

The new industrial intermediates necessary for the implementation of the process of the invention are the compounds of formula III and III' as well as their alkali metal, alkaline-earth metal and magnesium salts, in the form of diastereoisomer mixtures or separate diastereoisomers.

The compound of formula I is described in the French Patent No. 1,580,474 and is an important intermediate in the synthesis of well known esters having an insecticide activity as is described in French Patent No. 2,396,006.

In the following examples, there are described several preferred embodiments to illustrate the invention. However it should be understood that the invention is not intended to be limited to the specific embodiments.

EXAMPLE 1

Lactone of 1R,cis 2,2-dimethyl-3-formyl-cyclopropane-1-carboxylic acid or (1S-(1α, 2β, 5α))-6,6-dimethyl-4-oxo-3-oxabicyclo [3.1.0] hexan-2-ol STEP A: 1R,cis 2,2-dimethyl-3-(hydroxy-carboxy-methyl)-cyclopropane-1-carboxylic acid 13.2 ml of an aqueous solution of sodium hypochlorite at 47° chlorometric were added to a solution of 1 g of 1R,cis 2,2-dimethyl -3-(2-oxo-propyl)-cyclopropane-1-carboxylic acid in 10 ml of water. The mixture was stirred at ambient temperature for 2 hours and then 2.2 ml of the sodium hypochlorite solution were added. The mixture was stirred for 30 minutes and the oxidizing power of the medium was destroyed by the addition of an aqueous solution of sodium thiosulfate. The mixture was acidified to a pH of 2.5 by the addition of concentrated hydrochloric acid and was saturated with ammonium sulfate. Extraction took place with methylene chloride and ethyl acetate and the organic phase was dried and evaporated to dryness to obtain 0.6 g of the expected acid which was crystallized from isopropyl ether.

STEP B: Lactone of 1R,cis 2,2-dimethyl-3-formyl-cyclopropane-1-carboxylic acid 4 g of the acid of Step A, 54 ml of water, 26 ml of acetic acid and 40 ml of methylene chloride were mixed together and 16 ml of an aqueous solution of sodium hypochlorite at 48° chlorometric were introduced with stirring over about 30 minutes at ambient temperature. The mixture was stirred for 1 hour and then the oxidizing power of the medium was destroyed by the addition of an aqueous solution of sodium thiosulfate. The mixture was acidified to a pH of 2.5 by the addition of concentrated hydrochloric acid and saturated by addition of ammonium sulfate. Extraction took place with methylene chloride and after drying an evaporating the solvent, 2.68 g of the expected crude lactone were obtained. 2 g of the product were impasted in a water-toluene mixture, followed by separation and drying to obtain 1.6 g of the expected product melting at 113° C. and having a specific rotation of $[\alpha]_D^{20} = -110.5°$ (c=1% in DMF).

EXAMPLE 2

Lactone of 1R,cis 2,2-dimethyl-3-formyl-cyclopropane-1-carboxylic acid or (1S-(1α, 2β, 5α))-6,6-dimethyl-4-oxo-3-oxabicyclo [3.1.0] hexan-2-ol 20 mg of the acid of Step A of Example 1 and 1 ml of water were mixed together at ambient temperature and then 15 mg of potassium permanganate were added. The mixture was stirred at ambient temperature for 20 hours and the mixture was treated as in Step B of Example 1 with the exception of the acidification and the expected product was obtained with a yield of approximately 50%.

EXAMPLE 3

Lactone of 1R,cis 2,2-dimethyl-3-formyl-cyclopropane-1-carboxylic acid or (1S-(1α, 2β, 5α))-6,6-dimethyl-4-oxo-3-oxabicyclo [3.1.0.] hexan-2-ol 20 mg of the acid of Step A of Example 1 and 1 ml of water were mixed together at ambient temperature and then a sulfochromic mixture was added in slight excess. The mixture was stirred at ambient temperature for 20 hours and the mixture was treated as in Step B of Example 1 with the exception of the acidification, and the expected product was obtained with a yield of approximately 50%.

EXAMPLE 4

Lactone of 1R,cis 2,2-dimethyl-3-formyl-cyclopropane-1-carboxylic acid or (1S-(1α, 2β, 5α))-6,6-dimethyl-4-oxo-3-oxabicyclo [3.1.0] hexan-2-ol 20 mg of the acid of Step A of Example 1 and 1 ml of water were mixed together at ambient temperature and then 20 mg of periodic acid were added. The mixture was stirred at ambient temperature for 20 hours and the mixture was treated as in Step B of Example 1 with the exception of the acidification, and the expected product was obtained with a yield of approximately 10%.

EXAMPLE 5

Lactone of 1R,cis 2,2-dimethyl-3-formyl-cyclopropane-1-carboxylic acid or (1S-(1α, 2β, 5α))-6,6-dimethyl-4-oxo-3-oxabicyclo [3.1.0] hexan 2-ol 20 mg of the acid of Step A of Example 1 and 1 ml of water were mixed together at ambient temperature and then an excess of sodium perborate was added. The mixture was stirred at ambient temperature for 20 hours and the mixture was treated as in Step B of Example 1 with the exception of the acidification, and the expected product was obtained with a yield of approximately 10%.

EXAMPLE 6

Lactone of 1R,cis 2,2-dimethyl-3-formyl-cyclopropane-1-carboxylic acid or (1S-(1α, 2β, 5α))-6,6-dimethyl-4-oxo-3-oxabicyclo [3.1.0] hexan-2-ol 20 mg of the acid of Step A of Example 1 and 2 ml of methylene chloride were mixed together and 20 mg of manganese dioxide previously activated by drying (16 hours to 11° C.) were added. The mixture was refluxed with stirring for 5 hours and then cooled. Evaluation was carried out with thin layer chromatography and the yield of the expected product was approximately 10%.

EXAMPLE 7

Lactone of 1R,cis 2,2-dimethyl-3-formyl-cyclopropane-1-carboxylic acid or (1S-(1α, 2β, 5α))-6,6-dimethyl-4-oxo-3-oxabicyclo [3.1.0] hexan-2-ol 100 mg of the acid of Step A of Example 1 were mixed with 2 ml of water and 1 ml of acetic acid and 330 mg of sodium bismuthate were added at ambient temperature. Then was stirred for 24 hours, after which the expected product was identified and determined by HPLC in the reaction medium to obtain a quantity greater than 80% of expected product.

EXAMPLE 8

1R,cis 2,2-dimethyl-3-(hydroxy-carboxy-methyl)-cyclopropane-1-carboxylic acid 2.2 g of 1R,cis 2,2-dimethyl-3-(2-oxo-propyl)-cyclopropane-1-carboxylic acid and 4 ml of water were mixed together at 20° C. and then 11.7 ml of 2N sodium hydroxide and then a solution of 9.7 g of calcium hypochlorite at 65% titer in 30 ml of water were added at 0° to +5° C. The mixture was stirred for 1 hour at 0° to +2° C. and an aqueous solution of sodium thiosulfate at 20% was added in sufficient quantity to destroy the oxidizing power of the medium. Then concentrated hydrochloric acid was added until a pH of 1 to 2 was obtained and 15 g of ammonium sulfate were added. The mixture was stirred for 15 minutes, filtered and the filtrate was extracted with ethyl acetate. After drying, the solvent was evaporated to obtain 2.5 g of the expected acid in the form of a semi-crystallized product in a mixture with its lactone form.

EXAMPLE 9

1R,cis 2,2-dimethyl-3-(hydroxy-carboxy-methyl)-cyclopropane-1-carboxylic acid

Using the procedure of Example 8, 17.15 g of lithium hypochlorite instead of the solution of calcium hypochlorite were reacted to obtain 2.4 g of expected semi-crystallized product, constituting a mixture of the said product with its lactonic form.

EXAMPLE 10

1R,cis 2,2-dimethyl-3-(hydroxy-carboxy-methyl)-cyclopropane-1-carboxylic acid

Using the procedure of Example 8, 61 g of a 2.2M aqueous solution of sodium hypobromite instead of the solution of calcium hypochlorite were reacted to obtain 3.76 g of the expected crude product in the form of an oil constituted by a mixture of said product with its lactonic form.

EXAMPLE 11

Lactone of 1R,cis 2,2-dimethyl-3-formyl-cyclopropane-1-carboxylic acid 0.8 g of the acid of Step A of Example 1, 16 ml of water and 4.2 ml of 2N sodium hydroxide were mixed together with 2.4 ml of an aqueous solution of sodium hypochlorite. Then, 2 drops of acetic acid were added at ambient temperature and the mixture was stirred for 1 hour. Then, an aqueous solution of sodium thiosulfate was added until the oxidizing power disappeared. Then, concentrated hydrochloric acid was added until a pH of approximately 2.5 was obtained and finally 10 g of ammonium sulfate were added. Extraction took place with methylene chloride and the organic phase was dried and evaporated to dryness. The residue was crystallized from toluene to obtain 0.2 g of the expected product melting at 114.5° C. and having a specific rotation of $[\alpha]_D^{20} = -101°$ (c=1% in DMF).

EXAMPLE 12

Lactone of 1R,cis 2,2-dimethyl-3-formyl-cyclopropane-1-carboxylic acid 0.5 g of 1R,cis 2,2-dimethyl-3-(2-oxo-propyl)-cyclopropane-1-carboxylic acid, 6.5 ml of water and 15.6 ml of an aqueous solution of sodium hypochlorite at approximately 47° chlorometric were mixed together and the mixture was heated at 30° C. for 2 hours. 7 ml of the hypochlorite solution were added and the mixture was stirred at 50° C. for 3 hours. After cooling to 5° C., sodium thiosulfate was added until the oxidizing power disappeared, followed by acidification to pH 1 with concentrated hydrochloric acid and extraction with methylene chloride. The organic phase was dried and evaporated to dryness to obtain 0.215 g of the crude expected product which can be purified by crystallization from toluene. The crystals were identical to those obtained in the preceding example.

EXAMPLE 13

Lactone of 1R,cis 2,2-dimethyl-3-formyl-cyclopropane1-carboxylic acid 30 g of 1R,cis 2,2-dimethyl-3-(2-oxo-propyl)-cyclopropane-1-carboxylic acid and 60 ml of water were mixed together at ambient temperature and 119 ml of 2N sodium hydroxide were added. 433 ml of an aqueous solution of sodium hypochlorite at 51° chlorometric were added at 0° to +2° C. to the solution. The mixture was stirred for 90 minutes and then was mixed with a solution of 329 ml of acetic acid and 90 ml of water and 30 ml of dichloroethane. After stirring at ambient temperature, the mixture was treated with a solution of sodium thiosulfate until the oxidizing power was destroyed and brought to a pH of 3 by the addition of concentrated hydrochloric acid. Extraction took place with methylene chloride, followed by washing with water and drying to obtain 27 g of the crude crystallized expected product which was purified as indicated in Example 11 or 12.

EXAMPLE 14

Lactone of 1R,cis 2,2-dimethyl-3-formyl-cyclopropane-1-carboxylic acid

Using the procedure of Example 13, 3 g of 1R,cis 2,2-dimethyl -3-(2-oxo-propyl)-cyclopropane-1-carboxylic acid and 1.6 equivalents of 2N sodium hydroxide and 6 equivalents of sodium hypochlorite were reacted. The solution was mixed with a solution of 30 ml of water and 55 g of dihydrated mono-sodium phosphate and 30 ml of dichloroethane. The operation was continued as in Example 13 and the expected product was obtained with a yield of 64%.

EXAMPLE 15

Isolation of the diastereoisomers of 1R,cis 2,2-dimethyl-3-(hydroxycarboxymethyl)-cyclopropane-1-carboxylic acid and the correspondinq lactone or (1S-(1α, 2β, 5α))-6,6-dimethyl-4-oxo-3-oxabicyclo [3.1.0] hexan-2-carboxylic acid A mixture of diastereoisomers of one of the corresponding examples above was used with 30 g being treated for 1 hour at ambient temperature with 2 equivalents of 2N sodium hydroxide. After bringing to pH 1, extracting took place with ethyl acetate. The organic phase was evaporated to dryness and the residue which was a mixture of acids was crystallized from methylene chloride at 0° C. 13 g of the product was taken up in 10 volumes of N hydrochloric acid and taken to 50° C. for 1 hour. The mixture of lactones was extracted with ethyl acetate, evaporated to dryness and the residue was crystallized from 4 volumes of ethyl ether at 0° C. to obtain 1.8 g of one of the lactone diastereoisomers melting at 177° C. and having a specific rotation of $[\alpha]_D^{20} = -100°$ (c=1% in DMF).

NMR Spectrum (CDCl$_3$ 250 MHz): 1.20 (s) and 1.26 (s): CH$_3$ twin; 2.09 (d, J =6) and 2.38 (m): H$_1$ and H$_3$/cis cyclopropyls; 5.12 (d, J =6): —CH—0.

1.2 g of this enantiomer was taken up in 10 volumes of 2N sodium hydroxide. The mixture was stirred for 2 hours at ambient temperature. Then, the pH was taken to 1 by the addition of pure hydrochloric acid at 0° C., followed by extracting with ethyl acetate and evaporating to dryness. The residue was crystallized from an ethyl acetate/methylene chloride mixture to obtain 0.8 g of one of the acid diastereoisomers melting at 176° C. and having a specific rotation of $[\alpha]_D^{20} = +9°$ (c=1% in DMF).

NMR Spectrum (DMSO 250 MHz): 1.13 (s) and 1.25 (s): CH$_3$ twin; 1.32 (m) and 1.51 (d, J=8.5); H$_3$ and H$_1$ (cis cyclopropyls); 4.39 (d, J=10.5); —CHOH; 5.24 and 12.08: other mobile absorptions.

The other acid diastereoisomer was obtained by crystallizing the mixture of acids from 10 volumes of methylene chloride at 0° C. and crystallizing the product from an ethyl acetate methylene chloride mixture (5/15) which melted at 144° C. and a specific rotation of $[\alpha]_D^{20} = -82.3°$ (c =1% in DMF).

NMR Spectrum (DMSO 250 MHz): 1.09 (s) and 1.24 (s): CH$_3$ twin; 1.31 (m) and 1.45 (d, J =8.5): H$_3$ and H$_1$/cis cyclopropyls; 4.29 (d, J =10.5): CHOH (R or S).

The corresponding lactone was obtained by heating the acid for 2 hours at 50° C. in 10 volumes of N hydrochloric acid and then, after cooling, by extraction with methyl-ethyl-ketone and evaporation to dryness to obtain the product with a melting point of 100° C. and a specific rotation of $[\alpha]_D^{20} = -63.7°$ (c =1% in DMF).

NMR Spectrum (CDCl$_3$ 250 MHz): 1.23 (s): CH$_3$ twin; 2.08 (d, J =6) and 2.31 (d, J=6): H$_1$ and H$_3$/cis cyclopropyls; 4.71 (s): —CHO R or S; 8.36 (s): OH—.

Various modifications of the process of the invention may be made without departing from the spirit or scope thereof and it is to be understood that the invention is intended to be limited only as defined in the appended claims.

What we claim is:

1. A process for the preparation of a compound of the formula

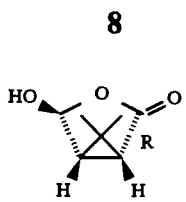

comprising reacting a compound of the formula

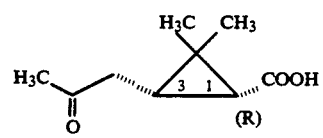

of 1R,cis configuration with an alkali metal, alkaline-earth metal or magnesium hypohalite to obtain a compound of the formula

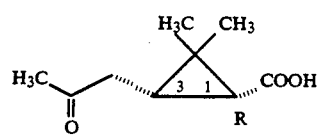

of 1R,cis configuration, also able to exist in the lactonic cyclized form

one or other form appearing as a mixture of diastereoisomers and in the form of an alkali metal, alkaline-earth metal or magnesium salt, optionally isolating the acid, then optionally isolating the diastereoisomers, then reacting the compound of formula III or III' in the form of a mixture of diastereoisomers or of separate diastereoisomers or its salt with an oxidizing agent to obtain the compound of formula I.

2. The process of claim 1 wherein the hypohalite is sodium, potassium, lithium, calcium or magnesium hypochlorite, hypobromite or hypoiodite.

3. The process of claim 1 wherein the hypohalite is sodium hypochlorite.

4. The process of claim 1 wherein at least 4 equivalents of hypohalite are used.

5. The process of claim 1 wherein the operation takes place at a temperature of −5° to +5° C. in aqueous phase.

6. The process of claim 1 wherein the reaction takes place in the presence of a basic agent.

7. The process of claim 6 wherein the basic agent is chosen from the group constituted by the alkali metal and alkaline-earth metal hydroxides.

8. The process of claim 6 wherein the basic agent is selected from the group consisting of sodium, potassium and calcium hydroxides.

9. The process of claim 1 wherein the oxidizing agent agent is chosen from the group consisting of halous acids, alkali metal, alkaline-earth metal and magnesium hypohalites, potassium, permanganate, chromic acid, periodic acid and alkali metal bismuthates.

10. The process of claim 9 wherein the hypohalous acid is obtained in situ from an alkali metal, alkaline-earth metal or magnesium hypohalite placed in acid medium.

11. The process of claim 9 wherein the oxidizing agent is hypochlorous acid obtained in situ from sodium hypochlorite placed in acid medium.

12. The process of claim 10 wherein the acid is chosen from the group consisting of lower alkanoic acids.

13. The process of claim 10 wherein the acid is selected from the group consisting of acetic and propionic acids, and solutions of phosphates, borates and acetates.

14. The process of claim 1 wherein the operation takes place without intermediate isolation of the compound of formula III or III'.

15. The process of claim 14 wherein the oxidizing agent is chosen from the group consisting of halous acids, alkali metal, alkaline-earth metal and magnesium hypohalites, potassium permanganate, chromic acid, periodic acid and alkali metal bismuthates.

16. The process of claim 14 wherein a quantity greater than 4 equivalents of a hypohalite is used.

17. The process of claim 16 wherein the hypohalite is sodium hypochlorite.

18. A compound selected from the group consisting of a formula

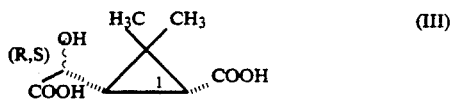

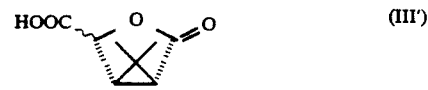

as well as their alkali metal, alkaline-earth metal or magnesium salts in the form of diastereoisomer mixtures or of separate distereoisomers.

* * * * *

UNITED STATES PATENT AND TRADEMARK OFFICE
CERTIFICATE OF CORRECTION

PATENT NO. : 5,278,322
DATED : January 11, 1994
INVENTOR(S) : FRANCIS BRION It is certified that error appears in the above-identified patent and that said Letters Patent is hereby corrected as shown below:

Column 8, line 25, replace the formula:

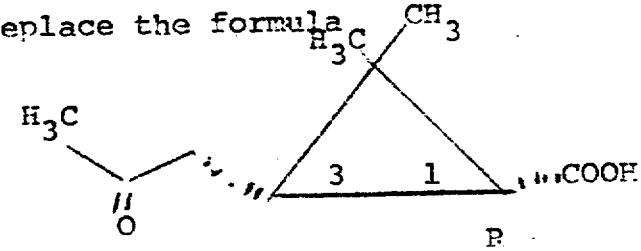

with the following formula:

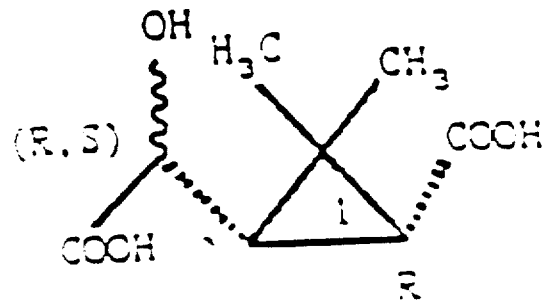

Signed and Sealed this

Eleventh Day of October, 1994

Attest:

BRUCE LEHMAN

Attesting Officer     Commissioner of Patents and Trademarks